(12) United States Patent
Burakowska-Meise et al.

(10) Patent No.: US 11,491,090 B2
(45) Date of Patent: Nov. 8, 2022

(54) SPHERICAL MICROPARTICLES WITH POLYESTER WALLS

(71) Applicant: BASF SE, Ludwigshafen am Rhein (DE)

(72) Inventors: Ewelina Burakowska-Meise, Ludwigshafen am Rhein (DE); Wolfgang Krause, Ludwigshafen am Rhein (DE); Patrick Leibach, Ludwigshafen am Rhein (DE); Karl Kolter, Ludwigshafen am Rhein (DE)

(73) Assignee: BASF SE

( * ) Notice: Subject to any disclaimer, the term of this patent is extended or adjusted under 35 U.S.C. 154(b) by 191 days.

(21) Appl. No.: 16/339,404

(22) PCT Filed: Oct. 4, 2017

(86) PCT No.: PCT/EP2017/075245
§ 371 (c)(1),
(2) Date: Apr. 4, 2019

(87) PCT Pub. No.: WO2018/065481
PCT Pub. Date: Apr. 12, 2018

(65) Prior Publication Data
US 2019/0231659 A1    Aug. 1, 2019

(30) Foreign Application Priority Data

Oct. 7, 2016   (EP) .................................... 16192882

(51) Int. Cl.
| | | |
|---|---|---|
| *A61K 8/11* | (2006.01) | |
| *A61K 9/50* | (2006.01) | |
| *C08L 67/03* | (2006.01) | |
| *A61Q 5/02* | (2006.01) | |
| *A61Q 13/00* | (2006.01) | |
| *A61K 8/85* | (2006.01) | |
| *A61Q 19/10* | (2006.01) | |
| *C11D 3/50* | (2006.01) | |
| *B01J 13/06* | (2006.01) | |
| *B01J 13/20* | (2006.01) | |
| *B01J 13/02* | (2006.01) | |
| *A61K 8/06* | (2006.01) | |
| *A61K 8/81* | (2006.01) | |
| *A61K 8/87* | (2006.01) | |
| *A61K 9/00* | (2006.01) | |

(52) U.S. Cl.
CPC .............. *A61K 8/11* (2013.01); *A61K 8/068* (2013.01); *A61K 8/8111* (2013.01); *A61K 8/8152* (2013.01); *A61K 8/85* (2013.01); *A61K 8/87* (2013.01); *A61K 9/5031* (2013.01); *A61K 9/5089* (2013.01); *A61Q 5/02* (2013.01); *A61Q 13/00* (2013.01); *A61Q 19/10* (2013.01); *B01J 13/02* (2013.01); *B01J 13/06* (2013.01); *B01J 13/206* (2013.01); *C11D 3/505* (2013.01); *A61K 9/007* (2013.01)

(58) Field of Classification Search
CPC .................................................. A61K 2800/56
See application file for complete search history.

(56) References Cited

U.S. PATENT DOCUMENTS

| | | | |
|---|---|---|---|
| 4,363,888 A | 12/1982 | Willison et al. | |
| 4,633,888 A | 1/1987 | Yoneyama | |
| 4,645,664 A | 2/1987 | Lange | |
| 5,817,721 A | 10/1998 | Warzelhan et al. | |
| 5,863,991 A | 1/1999 | Warzelhan et al. | |
| 5,880,220 A | 3/1999 | Warzelhan et al. | |
| 5,889,135 A | 3/1999 | Warzelhan et al. | |
| 6,018,004 A | 1/2000 | Warzelhan et al. | |
| 6,046,248 A | 4/2000 | Warzelhan et al. | |
| 6,111,058 A | 8/2000 | Warzelhan et al. | |

(Continued)

FOREIGN PATENT DOCUMENTS

| | | | |
|---|---|---|---|
| DE | 3428640 A1 | 2/1986 | |
| EP | 0397245 A2 * | 11/1990 | ........... A61K 8/0241 |

(Continued)

OTHER PUBLICATIONS

Ullman's Polymers and Plastics Products and Processes, 2016; WILEY-VCH, "Polyesters," pp. 791-816. (Year: 2016).*
Hawley's Condensed Chemical Dictionary, 15th ed., Lewis, Richard J. (editor), 2007, pp. 36 & 100. (Year: 2007).*
Brunner et al.; Performance of biodegradable microcapsules of poly(butylene succinate), poly(butylene succinate-co-adipate) and poly(butylene terephthalate-co-adipate as drug encapsulation systems, 2011, ELSEVIER; Colloids and Surfaces B: Biointerfaces, vol. 84, pp. 498-507. (Year: 2011).*

(Continued)

*Primary Examiner* — Tigabu Kassa
*Assistant Examiner* — Ivan A Greene
(74) *Attorney, Agent, or Firm* — Faegre Drinker Biddle & Reath LLP

(57) ABSTRACT

The present invention relates to compositions of spherical microparticles composed of a wall material and at least one cavity that comprises a gas and/or a liquid, which have pores on the surface thereof, wherein the spherical microparticles have a mean particle diameter of 10-600 μm and wherein at least 80% of those microparticles, the particle diameter of which does not deviate from the mean particle diameter of the microparticles of the composition by more than 20%, each have on average at least 10 pores, the diameter of which is in the range from $1/5000$ to $1/5$ of the mean particle diameter, and, furthermore, the diameter of each of these pores is at least 20 nm,
wherein the wall material consists of a composition comprising at least one aliphatic-aromatic polyester, and the wall material has a solubility at 25° C. of at least 50 g/l in dichloromethane, a method for the preparation thereof and also the use thereof.

12 Claims, No Drawings

(56) References Cited

U.S. PATENT DOCUMENTS

| | | | |
|---|---|---|---|
| 6,120,895 A | 9/2000 | Kowitz et al. | |
| 6,258,924 B1 | 7/2001 | Warzelhan et al. | |
| 6,353,084 B1 | 3/2002 | Warzelhan et al. | |
| 6,573,308 B1 | 6/2003 | Braun et al. | |
| 10,112,882 B2 | 10/2018 | Thrun et al. | |
| 2005/0069591 A1 | 3/2005 | Bernstein et al. | |
| 2011/0027376 A1* | 2/2011 | Boey | B01J 13/06 424/499 |
| 2011/0187029 A1 | 8/2011 | Dietrich et al. | |
| 2012/0312490 A1* | 12/2012 | Blum | D21H 17/53 162/164.7 |
| 2015/0111144 A1* | 4/2015 | Nair | G03G 9/08797 430/109.1 |
| 2016/0145459 A1 | 5/2016 | Klein et al. | |
| 2018/0230076 A1 | 8/2018 | Thrun et al. | |

FOREIGN PATENT DOCUMENTS

| | | | | |
|---|---|---|---|---|
| EP | 0467528 | A2 | 1/1992 | |
| EP | 2736973 | A1 | 6/2014 | |
| EP | 3002003 | A1 | 4/2016 | |
| EP | 3007815 | A1 | 4/2016 | |
| WO | WO-9209654 | A2 | 6/1992 | |
| WO | WO-9615173 | A1 | 5/1996 | |
| WO | WO-9615174 | A1 | 5/1996 | |
| WO | WO-9615175 | A1 | 5/1996 | |
| WO | WO-9615176 | A1 | 5/1996 | |
| WO | WO-9621689 | A2 | 7/1996 | |
| WO | WO-9621690 | A1 | 7/1996 | |
| WO | WO-9621691 | A1 | 7/1996 | |
| WO | WO-9621692 | A1 | 7/1996 | |
| WO | WO-9625446 | A1 | 8/1996 | |
| WO | WO-9625448 | A1 | 8/1996 | |
| WO | WO-9722409 | A1 * | 6/1997 | B01J 13/02 |
| WO | WO-9812242 | A1 | 3/1998 | |
| WO | WO-2006097354 | A1 | 9/2006 | |
| WO | WO-2010034710 | A1 | 4/2010 | |
| WO | 2013/017431 | A1 | 2/2013 | |
| WO | WO-2014198531 | A1 | 12/2014 | |
| WO | WO-2015070172 | A1 | 5/2015 | |
| WO | WO-2015165836 | A1 | 11/2015 | |
| WO | WO-2016050836 | A1 | 4/2016 | |

OTHER PUBLICATIONS

Wit et al.; "Biodegradation Behavior and Material Properties of Aliphatic/Aromatic Polyesters of Commercial Importance," Journal of Environmental Polymer Degradation, vol. 5, No. 2, 1997, pp. 81-89. (Year: 1997).*

El-Sherif et al. ("Development of a novel method for synthesis of a polymeric ultrasound contrast agent," Journal of Biomedical Materials Research Part A: An Official Journal of The Society for Biomaterials, 66.2 (2003): 347-355. (Year: 2003).*

European Search Report for EP Patent Application No. 16192882.5, dated Mar. 17, 2017, 3 pages.

Hu, et al., "Synthesis and Characterization of Polyfunctional Aziridine/ Polyester Microcapsules by Multiple Emulsion-Solvent Evaporation Method", Journal of Central South University of Technology, vol. 18, Issue 2, Apr. 2011, pp. 337-342.

Narita, et al., "Preparation of W/O/W microcapsule containing enzyme without alcohol", Colloids and Surfaces A: Physicochemical and Engineering Aspects, vol. 347, Issues 1-3, Sep. 5, 2009, pp. 187-191.

Qutachi, et al., "Injectable and porous PLGA microspheres that form highly porous scaffolds at body temperature", Acta Biomaterialia, vol. 10, Issue 12, Dec. 2014, pp. 5090-5098.

International Preliminary Reporton Patentability received for PCT Patent Application No. PCT/EP2017/075245, dated Apr. 18, 2019, 17 pages (10 pages of English Translation and 7 pages of Original Document).

International Search Report for PCT/EP2017/075245 dated Nov. 27, 2017.

Written Opinion of the International Searching Authority for PCT/EP2017/075245 dated Nov. 27, 2017.

* cited by examiner

SPHERICAL MICROPARTICLES WITH POLYESTER WALLS

CROSS-REFERENCE TO RELATED APPLICATIONS

This application is a national stage application (under 35 U.S.C. § 371) of PCT/EP2017/075245, filed Oct. 4, 2017, which claims benefit of European Application No. 16192882.5, filed Oct. 7, 2016, both of which are incorporated herein by reference in their entirety.

The present invention relates to a method for preparing spherical microparticles, to the fillable spherical microparticles obtainable by this method, and and also to the use thereof.

Microcapsules, like porous microparticles, are used as carrier for active substances, which as a result can be better processed, formulated, or released in a controlled manner.

Thus, in the medical sector, microparticles based on biopolymers for the controlled release of active compounds are known. In "Acta Biomaterialia" 10(2914) 5090-5098, porous microspheres having a scaffold made of a copolymer (PLGA) of lactic acid and hydroxyacetic acid (glycolic acid) and having a mean particle diameter of 84 μm are described.

Jian-Qing Hu et al, "Journal of Central South University of Technology", vol. 18, No. 2, (2011-04-01), pages 337-342, describes the preparation of microcapsules comprising a polyfunctional aziridine as capsule core. Such microcapsules are tight, and are intended to release the crosslinker as required, by destruction of the capsule wall. The capsules are formed from a w/o/w emulsion, by the oil phase comprising a polyester dissolved in dichloromethane, and the wall being formed by removal of the solvent. The wall material is a polyester made of dime-thylphthalate, glycol and 1,3-propanediol.

DE 3428640 teaches the production of microporous pulverulent polylactides and the use thereof for the controlled administration of active compounds.

Furthermore, WO 2015/070172 teaches porous microspheres made of PLGA, the pores of which have been loaded with proteins and the pores of which are closed by heating. The addition of magnesium carbonate or zinc carbonate to modify the pH brings about an improvement in the intake of the proteins.

Furthermore, US 2005/0069591 teaches porous microspheres made of a biodegradable polymer such as PLGA, which are prepared via a double water/oil/water emulsion. The microspheres are subsequently loaded with proteins.

EP 467 528 teaches polymeric carrier particles having particle sizes up to 250 μm and pores at the surface thereof, wherein the maximum pore size is 0.4 μm. The material of the carrier particles is in this case prepared by polymerization of styrene and a polyester of maleic anhydride/phthalic anhydride/propylene glycol. The polyester serves as crosslinker in this radical polymerization. The radical polymerization in this case is carried out as bulk polymerization, with the polyester being directly polymerized in the styrene.

The microporous polymers of the prior art are customarily loaded with medical active compounds or proteins and are intended to administer these in a controlled manner in the form of medicaments. Longer storage is not required in this case. Furthermore, such substances are hydrophilic.

If it is desired to provide aroma chemicals in a form that is readily handled, e.g. in the form of microparticles, other requirements must be met. Such microparticles should have good long-term stability, that is to say a good shelf life. For this, the microparticles themselves must be stable to the aroma chemicals, which of course are generally hydrophobic.

It was therefore an object of the present invention to provide microparticles which can be readily filled with an aroma chemical and subsequently closed. The resulting present aroma chemical preparations should have a good shelf life.

Accordingly, a method for preparing spherical microparticles was found, in which
a) an emulsion is prepared from an aqueous solution of a pore former as discontinuous phase and a continuous phase comprising a solution of at least one aliphatic-aromatic polyester in a water-immiscible solvent,
b) the w/o emulsion obtained in a) is emulsified in water in the presence of a dispersant to give a w/o/w emulsion having droplets with a mean size of 1-600 μm, and the water-immiscible solvent is removed at a temperature in the range from 20 to 80° C.,
c) the spherical microparticles formed in method step b) are separated off and optionally dried.

Furthermore, the spherical microparticles obtainable by this method, the use thereof as carrier for aroma chemicals, a method for the filling thereof with at least one aroma chemical and the filled spherical microparticles obtained thereby, and also aroma chemical preparations, were also found.

Furthermore, the use of the closed microparticle filled with at least one aroma chemical in perfumes, washing and cleaning agents, cosmetic agents, body care agents, hygiene articles, aroma compositions, food, food supplements, scent dispensers and fragrances was found, and also the use thereof for the controlled release of aroma chemicals.

Furthermore, compositions of spherical microparticles composed of a wall material and at least one cavity that comprises a gas and/or a liquid were found, which have pores on the surface thereof, wherein the spherical microparticles have a mean particle diameter of 10-600 μm, wherein the spherical microparticles have a mean particle diameter of 10-600 μm and wherein at least 80% of those microparticles, the particle diameter of which does not deviate from the mean particle diameter of the microparticles of the composition by more than 20%, each have on average at least 10 pores, the diameter of which is in the range from ⅕₀₀₀ to ⅕ of the mean particle diameter, and, furthermore, the diameter of each of these pores is at least 20 nm, wherein the wall material consists of a composition comprising at least one aliphatic-aromatic polyester, and the wall material has a solubility at 25° C. of at least 50 g/l in dichloromethane.

The statement regarding the state of matter of the substance contained in the cavity of the microparticle relates to 20° C. (room temperature) and 1 bar.

Furthermore, the following preferred embodiments were found:

1. A composition of spherical microparticles composed of a wall material and at least one cavity that comprises a gas and/or a liquid, which have pores on the surface thereof, wherein the spherical microparticles have a mean particle diameter of 10-600 μm and wherein at least 80% of those microparticles, the particle diameter of which does not deviate from the mean particle diameter of the microparticles of the composition by more than 20%, each have on average at least 10 pores, the diameter of which is in the range from ⅕₀₀₀ to ⅕ of the mean particle diameter, and, furthermore, the diameter of each of these pores is at least 20 nm, wherein the wall material consists of a composition comprising at least one aliphatic-aromatic polyester, and the wall material has a solubility at 25° C. of at least 50 g/l in dichloromethane.
2. The composition of spherical microparticles according to embodiment 1, wherein the aliphatic-aromatic polyester is an ester of an aliphatic dihydroxy compound esterified with a composition of aromatic dicarboxylic acid and aliphatic dicarboxylic acid.
3. The composition of spherical microparticles according to embodiment 1 or 2, wherein the aliphatic-aromatic polyester is selected from polybutylene azelate-co-butylene terephthalate (PBAzeT), polybutylene brassylate-co-butylene terephthalate (PBBrasT), polybutylene adipate terephthalate (PBAT), polybutylene sebacate terephthalate (PBSeT) and polybutylene succinate terephthalate (PBST).
4. The composition of spherical microparticles according to one of embodiments 1 to 3, wherein the composition forming the wall material comprises at least one polymer having a glass transition temperature or a melting point in the range from 45 to 140° C.
5. The composition of spherical microparticles according to one of embodiments 1 to 4, wherein the wall material consists of a composition comprising at least one aliphatic-aromatic polyester and also at least one further polymer selected from polyacrylate, polyamide, polycarbonate, polystyrene, aliphatic-aliphatic polyester, aromatic-aromatic polyester, polyolefin, polyurea and polyurethane.
6. The composition of spherical microparticles according to one of embodiments 1 to 5, wherein the wall material consists of a composition comprising 30 to 70 wt % of at least one aliphatic-aromatic polyester and also 30 to 70 wt % of at least one further polymer selected from polyacrylate, polyamide, polycarbonate, polystyrene, aliphatic-aliphatic polyester, aromatic-aromatic polyester, polyolefin, polyurea and polyurethane.
7. The composition of spherical microparticles according to one of embodiments 1 to 6, wherein the wall material consists of a composition comprising at least one aliphatic-aromatic polyester and also at least one aliphatic-aliphatic polyester.
8. The composition of spherical microparticles according to one of embodiments 1 to 7, wherein the wall material consists of a composition comprising at least one aliphatic-aromatic polyester and also at least one aliphatic-aliphatic polyester selected from PLA copolymers (polylactide and polylactic acid copolymers) and PLGA copolymers, especially polylactide copolymers.
9. A method for preparing a composition of spherical microparticles according to one of embodiments 1 to 8, wherein
   a) an emulsion is prepared from water or an aqueous solution of a pore former as discontinuous phase and a continuous phase comprising a solution of at least one aliphatic-aromatic polyester in a water-immiscible solvent,
   b) the w/o emulsion obtained in a) is emulsified in water in the presence of a dispersant to give a w/o/w emulsion having droplets with a mean size of 10-600 µm, and the water-immiscible solvent is removed at a temperature in the range from 20 to 80° C., preferably from 20 to 45° C.,
   c) the spherical microparticles formed in method step b) are separated off and optionally dried.
10. The method according to embodiment 9, wherein the continuous phase prepared under a) is a solution of at least one aliphatic-aromatic polyester and also at least one further polymer selected from polyacrylate, polyamide, polycarbonate, polystyrene, aliphatic-aliphatic polyester, aromatic-aromatic polyester, polyolefin, polyurea and polyurethane in a water-immiscible solvent.
11. The method according to embodiment 9 or 10, wherein the water-immiscible solvent is selected from dichloromethane, chloroform, ethyl acetate, n-hexane, cyclohexane, methyl-tert-butyl ether, pentane, diisopropyl ether and benzene, or mixtures of these solvents.
12. The method according to one of embodiments 9 to 11, wherein the emulsification to give the w/o/w emulsion in method step b) takes place with a stirrer for a period of 1-30 minutes.
13. The use of the composition of spherical microparticles according to one of embodiments 1 to 8, as carrier substance for filling with at least one aroma chemical.
14. A method for preparing an aroma chemical preparation, wherein the dried composition of spherical microparticles according to one of embodiments 1 to 8 is suspended in a liquid aroma chemical or in a solution of at least one aroma chemical, and subsequently kept at a temperature in the range from 40 to 80° C. for a period of 1 minute to 10 hours.
15. An aroma chemical preparation obtainable according to a method according to embodiment 14.
16. The use of the aroma chemical preparation according to embodiment 15, wherein it is used in an agent selected from perfumes, washing and cleaning agents, cosmetic agents, body care agents, hygiene articles, food, food supplements, scent dispensers or fragrances.
17. An agent comprising an aroma chemical preparation according to embodiment 15, in a proportion by weight of 0.01 to 99.9 wt % based on the total weight of the composition.
18. The use of the aroma chemical preparation according to embodiment 15 for the controlled release of aroma chemicals.
19. A method for preparing spherical microparticles, wherein
   a) an emulsion is prepared from water or preferably an aqueous solution of a pore former as discontinuous phase and a continuous phase comprising a solution of at least one aliphatic-aromatic polyester in a water-immiscible solvent,
   b) the w/o emulsion obtained in a) is emulsified in water in the presence of a dispersant to give a w/o/w emulsion having droplets with a mean size of 10-600 µm, and the water-immiscible solvent is removed at a temperature in the range from 20 to 80° C.,
   c) the spherical microparticles formed in method step b) are separated off and optionally dried.
20. The method according to embodiment 19, wherein the aliphatic-aromatic polyester is an ester of an aliphatic dihydroxy compound esterified with a composition of aromatic dicarboxylic acid and aliphatic dicarboxylic acid.
21. The method according to one of embodiments 19 and 20, wherein the aliphatic-aromatic polyester is selected from polybutylene azelate-co-butylene terephthalate (PBAzeT), polybutylene brassylate-co-butylene terephthalate (PBBrasT), polybutylene adipate terephthalate (PBAT), polybutylene sebacate terephthalate (PBSeT) and polybutylene succinate terephthalate (PBST).

22. The method according to one of embodiments 19 to 21, wherein at least one of the polymers contained in the continuous phase of a) has a glass transition temperature or a melting point in the range from 45 to 140° C.
23. The method according to one of embodiments 19 to 22, wherein one of the polymers contained in the continuous phase of a) is (partially) crystalline and has a melting point in the range from 45 to 140° C., or is amorphous and has a glass transition temperature in the range from 45 to 140° C.
24. The method according to one of embodiments 19 to 23, wherein the continuous phase prepared under a) consists essentially of the solution of an aliphatic-aromatic polyester in a water-immiscible solvent.
25. The method according to one of embodiments 19 to 24, wherein the continuous phase prepared under a) comprises the aliphatic-aromatic polyester and also at least one further dissolved polymer selected from polyacrylate, polyamide, polycarbonate, polystyrene, aliphatic-aliphatic polyester, aromatic-aromatic polyester, polyolefin, polyurea and polyurethane.
26. The method according to one of embodiments 19 to 25, wherein the continuous phase prepared under a) comprises the aliphatic-aromatic polyester and also at least one further polymer selected from polyacrylate, polyamide, polycarbonate, polystyrene, aliphatic-aliphatic polyester, aromatic-aromatic polyester, polyolefin, polyurea and polyurethane, wherein the ratio of aliphatic-aromatic polyester to the further polymer is 3/7 to 7/3.
27. The method according to one of embodiments 19 to 26, wherein the continuous phase prepared under a) comprises the aliphatic-aromatic polyester and also at least one dissolved aliphatic-aliphatic polyester.
28. The method according to one of embodiments 19 to 27, wherein the continuous phase prepared under a) comprises the aliphatic-aromatic polyester and also at least one further polymer selected from PLA copolymers (polylactide and polylactic acid copolymers) and PLGA copolymers, especially polylactide copolymers.
29. The method according to one of embodiments 19 to 28, wherein the water-immiscible solvent is selected from dichloromethane, chloroform, ethyl acetate, n-hexane, cyclohexane, methyl-tert-butyl ether, pentane, diisopropyl ether and benzene, or mixtures of these solvents.
30. The method according to one of embodiments 19 to 29, wherein the emulsification to give the w/o/w emulsion in method step b) takes place with a stirrer for a period of 1-30 minutes.
31. Spherical microparticles obtainable according to a process of embodiments 19 to 30.
32. The use of the spherical microparticles according to embodiment 31, as carrier substance for filling with at least one aroma chemical.
33. The method according to one of embodiments 19 to 30, wherein, subsequently,
   e) the dried spherical microparticles are suspended in a liquid aroma chemical or a solution of at least one aromachemical, and
   f) the microparticles obtained after e) are subsequently kept at a temperature in the range from 40 to 200° C., preferably 45 to 80° C. for a period of 1 minute to 10 hours.
34 An aroma chemical preparation obtainable according to embodiment 33.
35. The use of the aroma chemical preparation according to embodiment 34, wherein it is used in an agent selected from perfumes, washing and cleaning agents, cosmetic agents, body care agents, hygiene articles, food, food supplements, scent dispensers or fragrances.
36. An agent comprising an aroma chemical preparation according to embodiment 34, in a proportion by weight of 0.01 to 99.9 wt % based on the total weight of the composition.
37. The use of the aroma chemical preparation according to embodiment 34 for the controlled release of aroma chemicals.

The following related term, spherical microparticles, denotes a spherically formed polymer microparticle (or polymer microsphere). In one embodiment, this may be microcapsules, i.e. particles, in which an outer polymer layer encloses a core that is liquid or gaseous at room temperature.

Fillable spherical microparticles have openings on the surface thereof, such that an exchange of the material inside is possible. In the case of microcapsules, these are holes in the outer polymer layer, often also referred to as microcapsule shell or microcapsule wall. There are however also embodiments with porous spherical microparticles, which have a polymer matrix form. In these cases, this is a connected porous network that has openings at the surface of the microparticle.

Furthermore, there are embodiments of microparticles, the morphology of which has both.

The microparticles are formed by removal of the solvent in a w/o/w emulsion. In the first step, an emulsion of water droplets or droplets of the aqueous pore former solution is formed in the polyester solution. This w/o emulsion is in turn emulsified in water and the water-immiscible solvent is removed. By removing the solvent of the polyester, the latter becomes insoluble and becomes deposited at the surface of the water droplets or the aqueous pore former droplets. During this wall forming process, the pores are simultaneously formed, advantageously by the pore former.

Pore formers are for example compounds which release gas under the operating conditions of step b).

Pore formers are for example gas-releasing agents preferably selected from ammonium carbonate, sodium carbonate, ammonium hydrogencarbonate, ammonium sulfate, ammonium oxalate, sodium hydrogencarbonate, ammonium carbamate and sodium carbamate.

Furthermore, water-soluble low molecular weight compounds that create an osmotic pressure are suitable as pore formers. Upon removal of the water-insoluble solvent, a concentration gradient forms on account of the concentration gradient between the inner aqueous droplets with pore former and the outer aqueous disperse phase, which concentration gradient leads to migration of the water in the direction of the inner droplets and hence to formation of pores. Such pore formers are preferably selected from sugars such as monosaccharides, disaccharides, oligosaccharides and polysaccharides, urea, inorganic alkali metal salts such as sodium chloride and inorganic alkaline earth metal salts such as magnesium sulfate and calcium chloride. Particular preference is given to glucose and sucrose and urea.

Furthermore, polymers that are soluble in both phases, such as polyethylene glycol (PEG) and polyvinylpyrrolidone (PVP) are suitable as pore formers. Since these polymers are soluble in both phases, they migrate, because of diffusion, from the aqueous phase into the oil phase.

The methods for preparing the spherical microparticles always lead to a population of microparticles, as a result of which the term "composition of spherical microparticles" is also used.

The inventive microparticles have a mean particle diameter of D[4,3] from 10 to 600 μm (volume-weighted average, determined by means of light scattering). According to a preferred embodiment, the mean particle diameter D[4,3] is 1 to <100, preferably to 30 µm. According to a likewise preferred embodiment, the mean particle diameter D[4,3] is 100-500 µm.

The inventive microparticles have at least 10 pores at their surface, preferably at least 20 pores, the diameter of which is in the range from 1/5000 to 1/5 of the mean particle diameter, and furthermore the diameter of each of these pores is at least 20 nm. The microparticles preferably have on average at least 10 pores, preferably at least 20 pores, the diameter of which is in the range from 1/500 to 1/5 of the mean particle size, and furthermore the diameter of each of these pores is at least 20 nm. The microparticles preferred according to one embodiment, of mean particle diameter 100-500 µm, preferably have pores having a mean diameter in the range from 1/500 to 1/100 of the mean particle diameter. In each case, those microparticles of the composition of spherical microparticles whose particle diameter does not deviate from the mean particle diameter by more than 20% are taken into consideration. Of these, at least 80% meet the required number of pores at the particle surface.

According to the invention, an aliphatic-aromatic polyester is used. This term is understood to mean the esters based on aromatic dicarboxylic acids and aliphatic dihydroxy compounds. The aromatic dicarboxylic acids may also be used in a mixture with aliphatic dicarboxylic acids here. Aliphatic-aromatic polyesters are preferably polyesters based on aliphatic and aromatic dicarboxylic acids with aliphatic dihydroxy compound, what are referred to as semiaromatic polyesters. These polymers may be present individually or in the mixtures thereof.

The aliphatic-aromatic polyesters used according to the invention preferably have a glass transition temperature (determined using differential scanning calorimetry (DSC), DIN EN ISO 11357) or a melting point in the range from 45 to 140° C.

According to the invention, "aliphatic-aromatic polyesters" is also understood to mean polyester derivatives such as polyether esters, polyester amides or polyether ester amides and polyester urethanes (see EP application no. 10171237.0). The suitable aliphatic-aromatic polyesters include linear, non-chain-extended polyesters (WO 92/09654). Preference is given to chain-extended and/or branched aliphatic-aliphatic polyesters. The latter are known from WO 96/15173 to 15176, 21689 to 21692, 25446, 25448 or WO 98/12242, which are hereby explicitly incorporated by reference. Likewise considered are mixtures of different aliphatic-aromatic polyesters. Interesting recent developments are based on renewable raw materials (see WO-A 2006/097353, WO-A 2006/097354 and also WO 2010/034710).

Particularly preferred aliphatic-aromatic polyesters include polyesters comprising as essential components:
A) an acid component formed of
  a1) 30 to 99 mol % of at least one aliphatic dicarboxylic acid or the ester-forming derivatives thereof or mixtures thereof
  a2) 1 to 70 mol % of at least one aromatic dicarboxylic acid or the ester-forming derivative thereof or mixtures thereof, and
B) at least one diol component selected from $C_2$ to $C_{12}$ alkanediols
and
C) optionally a component selected from
  c1) a compound having at least three groups capable of ester formation,
  c2) a diisocyanate or polyisocyanate,
  c3) a diepoxide or polyepoxide, Aliphatic dicarboxylic acids and the ester-forming derivatives thereof (a1) that are generally considered are those having 2 to 18 carbon atoms, preferably 4 to 10 carbon atoms. They may be either linear or branched. However, it is also possible in principle to employ dicarboxylic acids having a greater number of carbon atoms, for example having up to 30 carbon atoms.

Examples include: oxalic acid, malonic acid, succinic acid, 2-methylsuccinic acid, glutaric acid, 2-methylglutaric acid, 3-methylglutaric acid, α-ketoglutaric acid, adipic acid, pimelic acid, azelaic acid, sebacic acid, brassylic acid, fumaric acid, 2,2-dimethylglutaric acid, suberic acid, diglycolic acid, oxalacetic acid, glutamic acid, aspartic acid, itaconic acid and maleic acid. These dicarboxylic acids or the ester-forming derivatives thereof may be used individually or as a mixture of two or more thereof.

It is preferable to employ succinic acid, adipic acid, azelaic acid, sebacic acid, brassylic acid or their respective ester-forming derivatives or mixtures thereof. It is particularly preferable to employ succinic acid, adipic acid or sebacic acid or the respective ester-forming derivatives thereof or mixtures thereof. Succinic acid, azelaic acid, sebacic acid and brassylic acid additionally have the advantage that they are obtainable from renewable raw materials.

Preference is given to the following aliphatic-aromatic polyesters: polybutylene azelate-co-butylene terephthalate (PBAzeT), polybutylene brassylate-co-butylene terephthalate (PBBrasT), and especially preferably: polybutylene adipate terephthalate (PBAT), polybutylene sebacate terephthalate (PBSeT) or polybutylene succinate terephthalate (PBST).

The aromatic dicarboxylic acids or the ester-forming derivatives thereof (a2) may be used individually or as a mixture of two or more thereof. Particular preference is given to using terephthalic acid or the ester-forming derivatives thereof such as dimethyl terephthalate.

Generally, the diols (B) are selected from branched or linear alkanediols having 2 to 12 carbon atoms, preferably 4 to 6 carbon atoms, or cycloalkanediols having 5 to 10 carbon atoms.

Examples of suitable alkanediols are ethylene glycol, 1,2-propanediol, 1,3-propanediol, 1,2-butanediol, 1,4-butanediol, 1,5-pentanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 2,2,4-trimethyl-1,6-hexanediol, especially ethylene glycol, 1,3-propanediol, 1,4-butanediol and 2,2-dimethyl-1,3-propanediol (neopentyl glycol); cyclopentanediol, 1,4-cyclohexanediol, 1,2-cyclohexanedimethanol, 1,3-cyclohexanedimethanol, 1,4-cyclohexanedimethanol or 2,2,4,4-tetramethyl-1,3-cyclobutanediol. Particular preference is given to 1,4-butanediol, especially in combination with adipic acid as component a1) and 1,3-propanediol, especially in combination with sebacic acid as component a1). 1,3-Propanediol also has the advantage that it is obtainable as a renewable raw material. Mixtures of different alkanediols may also be employed.

The preferred aliphatic-aromatic polyesters are characterized by a molecular weight (Mn) in the range from 1000 to 100 000, especially in the range from 9000 to 75 000 g/mol, preferably in the range from 10 000 to 50 000 g/mol.

Preferably, at least one of the polymers contained in the continuous phase of a) has a glass transition temperature or a melting point in the range from 45 to 140° C. If the polymer has a melting point, i.e. is (partially) crystalline, it preferably has a melting point in the range from 45 to 140° C. If the polymer is amorphous, it preferably has a glass transition temperature in the range from 45 to 140° C.

According to a preferred embodiment, the continuous phase prepared under a) consists essentially of the solution of an aliphatic-aromatic polyester in a water-immiscible solvent. The continuous phase particularly preferably consists, to at least 95 wt %, especially to at least 99 wt %, based on the continuous phase, of the solution of an aliphatic-aromatic polyester in a water-immiscible solvent.

According to a likewise preferred embodiment of the method, the continuous phase prepared under a) comprises the aliphatic-aromatic polyester and also at least one further dissolved polymer selected from polymers that are not aliphatic-aromatic polyesters.

Polymers that are not aliphatic-aromatic polyesters that may for example be mentioned are polyacrylate, polyamide, polycarbonate, polystyrene, aliphatic-aliphatic polyesters, aromatic/aromatic polyesters, polyolefin, polyurea and polyurethane. Preferred components in the mixtures with the at least one aliphatic-aromatic polyester are polyhydroxyacetic acid, PLA copolymers (polylactide and polylactic acid copolymers) and PLGA copolymers, and in this case especially polylactide copolymers. Polylactic acid having a molecular weight of 30 000 to 120 000 Dalton and a glass transition temperature ($T_g$) in the range from 50 to 65° C. is particularly suitable. Most particular preference is given to using amorphous polylactic acid, the D-lactic acid proportion of which is greater than 9%.

Polyhydroxyalkanoates are primarily understood to mean poly-4-hydroxybutyrates and poly-3-hydroxybutyrates, and also copolyesters of the aforementioned hydroxybutyrates with 3-hydroxyvalerates (P(3HB)-co-P(3HV)) or 3-hydroxyhexanoate.

The polyhydroxyalkanoates generally have a molecular weight $M_w$ of 30 000 to 1 000 000 and preferably of 100 000 to 600 000.

Preference is given according to the invention to mixtures of an aliphatic-aromatic polyester with one or more polymers which is (are) not an aliphatic-aromatic polyester, having a proportion by weight of the aromatic-aliphatic polyester of 30 to 99 wt % (based on the total weight of aliphatic-aromatic polyester and the polymer which is not an aliphatic-aromatic polyester). Preferably, the proportion of the aliphatic-aromatic polyester is 30 to 70, preferably 60, wt %, likewise preferably 20 to 50 wt % based on the total weight.

Preference is given to mixtures of an aliphatic-aromatic polyester with a further polymer which is not an aliphatic-aromatic polyester, especially the mixtures with aliphatic-aliphatic polyesters, in which the melting point of the aliphatic-aromatic polyester is at least 10 K, preferably at least 20 K, above the melting point of the further polymer, or the glass transition temperature of the aliphatic-aromatic polyester is at least 10 K, preferably at least 20 K, above the glass transition temperature of the further polymer. If the further polymer is an amorphous compound, then the melting point of the aliphatic-aromatic polyester is at least 10 K, preferably at least 20 K, above the glass transition temperature of the further polymer.

The composition of microparticles is prepared according to the double emulsion method.

Method Step a)

For this purpose, the aliphatic-aromatic polyester is dissolved in a water-immiscible solvent.

Water-immiscible means that the solvent has a solubility in water, at a temperature of 20° C. and a pressure of 1 bar, of ≤90 g/l. Furthermore, the water-immiscible solvent preferably has a boiling point of at least 30° C.

According to the general knowledge of those skilled in the art, solvents are chemically inert to the substances to be dissolved therein; that is to say, they merely serve for dilution or dissolution. Radically-polymerizable monomers are not solvents in the context of the invention.

Preference is given to aprotic non-polar and aprotic polar solvents or solvent mixtures, which have a water solubility of <90 g/l (at 20° C.).

Preferred solvents are for example dichloromethane, chloroform, ethyl acetate, n-hexane, cyclohexane, methyl-tert-butyl ether, pentane, diisopropyl ether and benzene, or mixtures of two or more of these solvents with one another. Dichloromethane is particularly preferred.

Furthermore, solvent mixtures which form an azeotrope, the boiling point of which is in the range from 20 to 80° C., are suitable. For example, mention may be made of the azeotrope of hexane and methyl ethyl ketone (MEK) in the weight ratio of 72:28.

As a rule, the polyester is used as 1 to 50 wt % solution in the water-immiscible solvent. This is preferably, in the polyester solution, a 2 to 30 wt %, especially a 5 to 20 wt % solution in the water-immiscible solvent.

Preference is given to selecting an emulsion formed of a solution of at least one aliphatic-aromatic polyester and the at least one further polymer. The solution used in this case may be obtained by mixing the individual polymer solutions or by co-dissolving a polymer mixture. The aliphatic-aromatic polyester or the mixture thereof with the at least one further polymer is the wall material of the subsequent microparticle. The wall material of the microparticle has a solubility at 25° C. and 1 bar of at least 50 g/l in dichloromethane.

In this polyester solution, water or an aqueous solution of the pore former is emulsified in method step a).

The aqueous solution of the pore former is preferably a 0.1 to 10 wt % aqueous solution of the pore former, especially of a pore former selected from ammonium hydrogencarbonate and ammonium carbonate. Particular preference is given to ammonium carbonate, especially a 0.1 to 1 wt % solution of ammonium carbonate in water.

0.1 to 10 parts by weight of the pore former are used, based on the aliphatic-aromatic polyester. 1 to 5 parts by weight of the pore former are preferably used, based on the aliphatic-aromatic polyester. 1.5 to 3 parts by weight of the pore former are especially used, based on the aliphatic-aromatic polyester.

The emulsification in method step a) is carried out using a disperser (rotor-stator or rotor-rotor). For example, homogenizers or dispersing machines having a high shear energy are suitable for preparing the w/o emulsion. The mean droplet size of the emulsion droplets is 0.2 to 30 µm.

The w/o emulsion prepared in method step a) may optionally be stabilized with a dispersant. Dispersants suitable for w/o emulsions are generally known and are mentioned in EP 3 007 815, the teaching of which is hereby expressly incorporated by reference.

Method Step b.)

The emulsification to give the w/o/w emulsion in method step b) is carried out by stirring or shearing in the presence of a dispersant.

An aqueous solution of the dispersant may be metered in to the w/o emulsion here. The dispersant is preferably initially charged in the form of an aqueous solution and the w/o emulsion is metered in.

Depending on the energy input, it is possible to control the droplet size. Furthermore, the dispersant described below influences the size of the emulsion droplets in equilibrium.

Larger droplets with a mean droplet size of 100 to 600 μm are obtained with customary stirrers.

Suitable stirrer types include, e.g. propeller stirrers, impeller stirrers, disk stirrers, vane stirrers, anchor stirrers, pitched-blade stirrers, cross-beam stirrers, helical stirrers, and screw stirrers. It is possible in this case to input sufficient shearing energy by vigorous stirring to achieve droplet sizes of 10 to <100 μm, preferably to 50 μm.

Should even higher energy input be intended, it may be advantageous to use apparatus for generating a shear field.

The shear energy input can be directly derived from the power consumption of the apparatus for generating a shear field. Thus, the shear energy input into the w/o/w emulsion is preferably 250 to 25 000 Watt·h/m$^3$ batch size. Particular preference is given to an energy input of 500 to 15 000, especially 800 to 10 000 Watt·h/m$^3$ batch size, calculated based on the motor current.

Suitable apparatus for generating a shear field are comminuters operating according to the rotor-stator principle, such as toothed ring dispersing machines, colloid and corundum disk mills, and also high-pressure and ultrasound homogenizers. Preference is given to the use of toothed ring dispersing machines operating according to the rotor-stator principle for generating the shear field. The diameter of the rotors and stators is customarily in the range between 2 cm and 40 cm, depending on machine size and dispersing performance. The speed of rotation of such dispersing machines is generally in the range from 500 to 20 000 rpm, depending on the construction type. Of course, machines with large rotor diameters rotate at the lower end of the rotation speed range, while machines with small rotor diameters are usually operated at the upper end of the rotation speed range. The distance of the rotating parts from the stationary parts of the dispersing apparatus is generally 0.1 to 3 mm.

According to a preferred embodiment, the final size of the emulsion droplets of the w/o/w emulsion should be a mean diameter D[4,3] (determined by means of light scattering) of 100 to 600 μm. This final size is generally achieved just by stirring.

According to a likewise preferred embodiment, the final size of the emulsion droplets of the w/o/w emulsion should have a mean diameter of 10 to 100 μm, preferably 10 to 30 μm. This final size is customarily achieved by means of shearing.

The w/o/w emulsion is prepared in the presence of a dispersant. Suitable dispersants are for example cellulose derivatives such as hydroxyethylcellulose, methylhydroxyethylcellulose, methylcellulose and carboxymethylcellulose, polyvinylpyrrolidone, copolymers of vinylpyrrolidone, gelatin, gum arabic, xanthan, casein, polyethylene glycols, and partially-hydrolyzed polyvinyl acetates (polyvinyl alcohols) and also methylhydroxypropylcellulose, and also mixtures of the above. Preferred organic neutral protective colloids are partially hydrolyzed polyvinyl acetates (polyvinyl alcohols) and also methyl hydroxy($C_1$-$C_4$)alkyl celluloses. Particular preference is given to polyvinyl alcohols (PVAs) with a degree of hydrolysis of 79% to 99.9%. In addition, PVA copolymers, as described in WO 2015/165836, are also suitable.

Methyl hydroxy($C_1$-$C_4$)alkyl celluloses are understood to mean methyl hydroxy($C_1$-$C_4$)alkyl celluloses of a wide variety of degrees of methylation and also degrees of alkoxylation. The preferred methyl hydroxy($C_1$-$C_4$)alkyl celluloses have an average degree of substitution DS of 1.1 to 2.5 and a molar degree of substitution MS of 0.03 to 0.9.

Suitable methyl hydroxy($C_1$-$C_4$)alkyl celluloses are for example methyl hydroxyethyl cellulose or methyl hydroxypropyl cellulose. Methyl hydroxypropyl cellulose is particularly preferred. Polyvinyl alcohols are especially preferred.

In order to stabilize the w/o/w emulsion, the dispersant is added to the aqueous phase. According to a preferred embodiment, carboxy-modified anionic PVA (having a degree of hydrolysis of 85 to 90 mol % and a viscosity of 20.0 to 30.0 mPa*s and proportion of carboxyl groups of 1 to 6 mol %) is used as 0.1 to 5.0 wt % aqueous solution. Particular preference is given to aqueous solutions having a PVA content of 0.3 to 2.5 wt %, especially solutions having a PVA content of 0.5 to 1.5 wt %.

According to a preferred method variant, in method step b) the emulsification to give the w/o/w emulsion is carried out with a stirrer at a stirring speed of 5000 to 15 000 rpm over a period of 1-30 minutes. The droplets produced thereby have a mean diameter of 0.2 to 30 μm.

According to a further preferred method variant, the emulsion is prepared at a stirring speed of 100-1000 rpm over a period of 1-30 minutes. The mean diameter of the droplets produced thereby is 100 to 600 μm.

During the emulsification, and optionally thereafter, the mixture is kept at a temperature in the range from 20 to 80° C. The temperature of the mixture is preferably selected such that it is below the glass transition temperature of the lowest softening amorphous polymer or below the melting point of the lowest melting crystalline polymer of the composition that forms the wall material. Higher temperatures are possible, but they may lead to partial closure of the pores over too long a period. The mixture is preferably kept at a temperature in the range from 20 to 45° C., especially from 20 to <40° C. Optionally, a vacuum may additionally be applied.

Both measures, the stirring/shearing and also the temperature, lead to the water-immiscible solvent of the at least one aliphatic-aromatic polyester evaporating and the microparticles being left behind.

Provided that it is a solvent having a vapor pressure ≥450 hPa at 20° C., it is sufficient to stir the w/o/w emulsion obtained in b) at room temperature, 20° C. Depending on the amount of the solvent and the ambient temperature, such an approach lasts a few hours. Depending on the solvent, it is possible to remove the solvent by raising the temperature to a temperature of up to 80° C. and/or by applying a slight vacuum.

For example, with solvents such as dichloromethane, according to a preferred embodiment the following is selected: 10 hours stirring at room temperature with 100 l/hour of nitrogen flow in a 2 l vessel, or 3 hours stirring at 45° C. jacket temperature with 100 l/hour of nitrogen flow in a 2 l vessel.

With solvents such as ethyl acetate, according to a further preferred embodiment the following is selected: 6 hours stirring at 60° C. with 100 l/hour of nitrogen flow.

In the course of the removal of the water-immiscible solvent, pore formation is observed in the walls of the microparticles.

The microparticles formed by removal of the water-immiscible solvent are removed in method step c) and preferably dried. "Dried" is understood to mean that the microparticles comprise a residual amount of water of ≤5 wt %, preferably ≤1 wt %, based on the microparticles. The drying may for example be carried out in a stream of air and/or by applying a vacuum, optionally in each case with heating. This may be carried out, depending on the size of the capsules, by means of convective dryers such as spray dryers, fluidized bed and cyclone dryers, contact dryers such as pan dryers, contact belt dryers, vacuum drying cabinet or radiative dryers such as infrared rotary tube dryer and microwave mixing dryer.

The spherical microparticles obtained in this way are also a subject of the present invention. They are characterized in that they are easy to fill, in that they are for example suspended in a solution.

The inventive composition consists of spherical microparticles constructed of wall material and at least one cavity, and having pores at their surface.

According to a preferred embodiment, the inventive spherical microparticles having a particle size in the range from 100 to 600 μm have a bulk density (determined according to DIN EN ISO 60: 1999) of 0.1 to 0.5 g/cm$^3$, preferably 0.15-0.4 g/cm$^3$, especially of 0.15 to 0.3 g/cm$^3$.

The inventive spherical microparticles are used as carrier substance for filling with an aroma chemical, preferably a fragrance, preferably in a solvent or diluent.

An "aroma chemical" is a generic term for compounds which may be used as "fragrance" and/or as "flavoring".

In the context of the present invention, "fragrance" is understood to mean natural or synthetic substances having intrinsic odor.

In the context of the present invention, "flavoring" is understood to mean natural or synthetic substances having intrinsic flavor.

In the context of the present invention, "odor" or "olfactory perception" is the interpretation of the sensory stimuli which are sent from the chemoreceptors in the nose or other olfactory organs to the brain of a living being. The odor can be a result of sensory perception by the nose of fragrances, which occurs during inhalation. In this case, the air serves as odor carrier.

In the context of the present invention, a "perfume" is a mixture of fragrances and carriers such as, in particular, an alcohol.

In the context of the present invention, a "perfume composition" is a perfume comprising different amounts of individual components harmoniously balanced with one another. The properties of the individual constituents are employed in order to achieve a new overall image in the combination, wherein the characteristics of the ingredients retire into the background but without being suppressed.

In the context of the present invention, a "perfume oil" is a concentrated mixture of several fragrances which are employed, for example, in alcoholic solutions, for perfuming different products.

In the context of the present invention, a "solvent for fragrance" serves as the diluent of the fragrances to be used according to the invention or the fragrance composition according to the invention but without having any intrinsic odorous properties. Some solvents also have fixing properties.

The fragrance, or a mixture of several fragrances, may be admixed to 0.1 to 99 wt % with a diluent or solvent. Preference is given to at least 40 wt % solutions, more preferably at least 50 wt % solutions, further preferably at least 60 wt % solutions, more preferably at least 70 wt % solutions, particularly preferably at least 80 wt % solutions, especially preferably at least 90 wt % solutions, preferably in olfactorily acceptable solutions.

Preferred olfactorily acceptable solvents are ethanol, isopropanol, dipropylene glycol (DPG), 1,2-propylene glycol, 1,2-butylene glycol, glycerol, diethylene glycol monoethyl ether, diethyl phthalate (DEP), 1,2-cyclohexane dicarboxylic acid diisononyl ester, isopropyl myristate (IPM), triethyl citrate (TEC), benzyl benzoate (BB) and benzyl acetate. In this case, preference is given in turn to ethanol, diethyl phthalate, propylene glycol, dipropylene glycol, triethyl citrate, benzyl benzoate and isopropyl myristate.

Fragrances:

Inventive microparticles comprise at least one fragrance, preferably 2, 3, 4, 5, 6, 7, 8 or more fragrances, which are for example selected from:

alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably having a cis-isomer content of more than 60 wt %) (Hedione[9], Hedione HC[9]), 4,6,6,7,8,8-hexamethyl-1,3,4,6,7,8-hexahydrocyclopenta[g]benzopyran (Galaxolide[3]), tetrahydrolinalool (3,7-dimethyl-octan-3-ol), ethyl linalool, benzyl salicylate, 2-methyl-3-(4-tert-butylphenyl)propanal (Lilial[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styralyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenone[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalide[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolene[1]), cis-3-hexenyl acetate, trans-3-hexenyl acetate, trans-2-cis-6-nonadienol, 2,4-dimethyl-3-cyclohexenecarboxaldehyde (Vertocitral[1]), 2,4,4,7-tetramethyl-act-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone[1951 5]), 3,3,5-trimethylcyclohexyl acetate (preferably with a content of cis-isomers of 70 wt %) or more and 2,5,5-trimethyl-1,2,3,4,4a,5,6,7-octahydronaphthalen-2-ol (Ambrinol S[1]). In the context of the present invention, the fragrances mentioned above are accordingly preferably combined with mixtures according to the invention.

If trade names are specified above, these refer to the following sources: ≠[1] Trade name of Symrise GmbH, Germany;

[2] Trade name of Givaudan AG, Switzerland;

[3] Trade name of International Flavors & Fragrances Inc., USA;

[5] Trade name of Danisco Seillans S. A., France;

[9] Trade name of Firmenich S. A., Switzerland;

[10] Trade name of PFW Aroma Chemicals B.V., The Netherlands.

Further fragrances with which the (E/Z)-cyclopentadecenylcarbaldehydes (I)-(III) may be combined, for example, to give a fragrance composition are found, for example, in S. Arctander, Perfume and Flavor Chemicals, Vol. I and II, Montclair, N. J., 1969, Author's edition or K. Bauer, D. Garbe and H. Surburg, Common Fragrance and Flavor Materials, 4th. Ed., Wiley-VCH, Weinheim 2001. Specifically, the following may be mentioned:

extracts from natural raw materials such as essential oils, concretes, absolutes, resins, resin-olds, balsams, tinctures such as e.g.

ambra tincture; amyris oil; angelica seed oil; angelica root oil; anise oil; valerian oil; basil oil; tree moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; lerrion oil; copaiba balsam; copaiba balsam oil; coriander oil; costus root oil; cumin oil; cypress oil; davana oil; dill oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil, helichrysum absolute; helichrysum oil; ginger oil; iris root absolute; iris root oil; jasmine absolute; calamus oil; camellia oil blue; camellia oil roman; carrot seed oil; cascarilla oil; pine needle oil; spearmint oil; cumin oil; labdanum oil; labdanum absolute; labdanum resin; lavandin absolute; lavandin oil; lavender absolute; lavender oil; lemon grass oil; lovage oil; lime oil distilled; lime oil pressed; linalool oil; litsea cubeba oil; laurel leaf oil; macis oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flow-er oil; neroli oil; olibanum absolute; olibanum oil; opopanax oil; orange blossom absolute; orange oil; oregano oil; palmarosa oil; patchouli oil; perilla oil; Peruvian balsam oil; parsley leaf oil; parsley seed oil; petitgrain oil; peppermint oil; pepper oil; allspice oil; pine oil; poley oil; rose absolute; rosewood oil; rose oil; rosemary oil; sage oil dalmatian; sage oil Spanish; sandalwood oil; celery seed oil; spike lavender oil; star anis oil; styrax oil; tagetes oil; fir needle oil; tea tree oil; turpentine oil; thyme oil; tolu balsam; tonka absolute; tuberose absolute; vanilla extract; vio-let leaf absolute; verbena oil; vetiver oil; juniper berry oil; wine yeast oil; vermouth oil; winter-green oil; ylang oil; ysop oil; civet absolute; cinnamon leaf oil; cinnamon bark oil; and fractions thereof or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-3-hexene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; (E/Z)-ethyl-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl and diethyl acetals of geranial, neral, 7-hydroxy-3,7-dimethyloctanal;

the cyclic terpene alcohols such as e.g. menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1- ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; cis-3-methylpent-2-en-1-yl-cyclopent-2-en-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; cyclohexadec-5-en-1-one; 6,7-dihydro-1,1,2,3,3-pentamethyl-4(5H)-indanone; 8 cyclohexadecen-1-one; 7-cyclohexadecen-1-one; (7/8)-cyclohexadecen-1-one; 9 cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl(2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-ylacetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6 indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis and trans-methyl dihydrojasmonate; cis and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phe-nylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl N-methylanthranilate; Schiffs bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis and trans-11-pentadecen-1,15-olide; cis and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Furthermore, compounds as described in PCT/EP2015/072544 are suitable as fragrances.

Particular preference is given to mixtures of L-menthol and/or DL-menthol, L-menthone, L-menthyl acetate, which are highly sought-after as analogs or substitutes for what are referred to as synthetic dementholized oils (DMOs). The mixtures of these minty compositions are preferably used in the ratio L-menthol or DL-menthol 20-40 wt %, L-menthone 20-40% and L-menthyl acetate 0-20%.

The present invention further relates to a method for filling and closing the microparticles.

The spherical microparticles are filled by the spherical microparticles being suspended in a liquid aroma chemical or solution of an aroma chemical, preferably of a fragrance. In order to prepare the suspension, for example magnetic stirrers, rollers, shakers, or various wall-adjacent stirring members (e.g. anchor stirrer, helical stirrer) are suitable. The duration of the mixing procedure is dependent on the solution of the aroma chemical and is generally from 5 minutes to 12 hours.

The suspending is for example carried out over a period of several hours, preferably for longer than 1 hour, for example 5 hours, by mixing at room temperature. Longer suspending is possible but after a certain point no further uptake of the loading will occur.

According to the invention, the spherical microparticles are filled by e) the spherical microparticles being suspended in a liquid aroma chemical or a solution of at least one aroma chemical, and f) subsequently, the microparticles obtained after e) being kept at a temperature in the range from 45 to 200° C. over a period of 1 minute to 10 hours, preferably at a temperature in the range from 40 to 140° C., preferably from 45 to 80° C., over a period of 1 hour to 10 hours, and g) optionally the spherical microparticles subsequently being removed.

Preferably, 1 part by weight of spherical microparticles is suspended in 1 to 5 parts by weight, preferably 1 to 3 parts by weight, of the aroma chemical or the solution thereof.

The suspension obtained after e) is generally kept at a temperature in the range from 45 to 200° C. for 1 minute to 10 hours. It is also even possible to close the microcapsules from 40° C. The suspension is preferably kept at a temperature in the range from 40 to 140° C., especially from 45 to 80° C. for 1 hour to 10 hours.

According to a preferred embodiment, spherical microparticles consisting of a polymer material made of 30 to 70 wt % PBAT and 30 to 70 wt % PLA are selected. These microparticles are mixed for at least 1 hour with at least one liquid aroma chemical or a solution of at least one aroma chemical, and subsequently heated to a temperature in the range from 55 to 70° C. and stirred at this temperature for at least 3 hours.

Preferably, spherical microparticles consisting of a polymer material made of 55 wt % PBAT and 45 wt % PLA are selected. After filling, these microparticles are heated to a temperature of 60° C. and stirred at this temperature for 5 hours. Thereafter, the suspension is cooled to room temperature and the filled microparticles are removed.

It is assumed that the filled microparticles are closed by coalescence of the pores, by the suspension, depending on the polymer of the microparticle that forms the wall material, being heated to above its melting point or to above its glass transition temperature when it does not have a melting point. Provided the wall material is a composition of at least two polymers, the same principle applies wherein the values of both polymers are taken into consideration. Furthermore, the present invention relates to a method for preparing an aroma chemical preparation, in which the spherical microparticles obtained according to the method are suspended in a solution of at least one aroma chemical, and are subsequently kept at a temperature in the range from 40 to 200° C., preferably from 45 to 80° C., for a period from 1 minute to 10 hours.

The present application relates to the spherical microparticles obtained by this method and also the use of the filled microparticles obtained by filling and closing, in agents selected from perfumes, washing and cleaning agents, cosmetic agents, body care agents, hygiene articles, food, food supplements, scent dispensers and fragrances.

Furthermore, it relates to the use of the spherical microparticles or the aroma chemical preparation, wherein it is used in an agent selected from perfumes, washing and cleaning agents, cosmetic agents, body care agents, hygiene articles, food, food supplements, scent dispensers or fragrances.

The filled spherical microparticles according to the invention are suitable for the controlled release of aroma chemicals.

Optionally, the closed and filled microparticles are removed from the solution of aroma chemical that was added in excess. The methods suitable therefor are for example filtration, centrifugation, decanting, vacuum distillation and spray drying.

It is optionally advantageous to remove any residual water present from the microparticles. This may be achieved for example by rinsing with ethanol or acetone, and/or blowing the microparticles dry with an inert gas such as air, nitrogen or argon. Optionally, for this purpose, pre-dried and/or preheated inert gases may be used. The filled microparticles are preferably subsequently rinsed, preferably with aqueous propanediol solution, for example as 10 wt % solution.

Generally known drying methods may be used for the drying. For example, the particles may be dried by means of convective dryers such as spray dryers, fluidized bed, cyclone dryers, contact dryers such as pan dryers, contact belt dryers, vacuum drying cabinet or radiative dryers such as infrared rotary tube dryer and microwave mixing dryer.

The inventive spherical microparticles filled with an aroma chemical or the solution of an aroma chemical, preferably a fragrance or a solution of a fragrance, may be incorporated into a variety of products or applied to such products. Such agents comprise the spherical microparticles or an aroma chemical preparation preferably in a proportion by weight of 0.01 to 99.9 wt % based on the total weight of the composition.

Spherical microparticles according to the invention can be used in the production of perfumed articles. The olfactory properties and also the physical properties and the non-toxicity of the inventive microparticles highlight their particular suitability for the intended uses mentioned.

The use of the microparticles proves to be particularly advantageous in conjunction with top notes of compositions, for example in perfume compositions comprising dihydrorosan, rose oxide or other readily volatile fragrances, e.g. iso-amyl acetate, prenyl acetate or methylheptenone. The release of the important, sought-after top notes is effectively delayed thereby. The fragrance or aroma compositions are accordingly metered in at the suitable point in the requisite amounts. In the mint compositions of L-menthol, DL-menthol, L-menthone and L-menthyl acetate described, aside from the aroma effect a cooling effect is applied in a targeted manner, e.g. in chewing gums, confectionery, cosmetic products, and technical applications such as in textiles or superabsorbers. A further advantage lies in the high material compatibility of the microparticles, even with reactive or unstable components such as aldehydes, esters, pyrans/ethers, which may exhibit secondary reactions on the surfaces.

The positive properties contribute to the fact that the fragrances used according to the invention and the fragrance compositions according to the invention are particularly preferably used in perfume products, body care products, hygiene articles, textile detergents and in cleaners for solid surfaces.

The perfumed article is e.g. selected from perfume products, body care products, hygiene articles, textile detergents and cleaners for solid surfaces. Preferred perfumed articles according to the invention are also selected from among:
perfume products selected from perfume extracts, Eau de Parfums, Eau de Toilettes, Eau de Colognes, Eau de Solide, Extrait Partum, air fresheners in liquid form, gel-like form or a form applied to a solid carrier, aerosol sprays, scented cleaners and scented oils;
body care products selected from aftershaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, hair shampoo, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics such as e.g. eye shadows, nail varnishes, make-ups, lipsticks, mascara, toothpaste, dental floss;
hygiene articles selected from candles, lamp oils, joss sticks, propellants, rust removers, perfumed freshening wipes, armpit pads, baby diapers, sanitary towels, toilet paper, cosmetic wipes, pocket tissues, dishwasher deodorizer;
cleaners for solid surfaces selected from perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners;
textile detergents selected from liquid detergents, powder detergents, laundry pretreatments such as bleaches, soaking agents and stain removers, fabric softeners, washing soaps, washing tablets.

According to a further aspect, the fragrances used according to the invention and the fragrance compositions according to the invention are suitable for use in surfactant-containing perfumed articles. This is because fragrances and/or fragrance compositions with a rose top note and pronounced naturalness are often sought—especially for the perfuming of surfactant-containing formulations such as, for example, cleaners (in particular dishwashing compositions and all-purpose cleaners).

According to a further aspect, fragrances used according to the invention and fragrance compositions according to the invention can be used as agents for providing (a) hair or (b) textile fibers with a rosy odor note.

The fragrances to be used according to the invention and fragrance compositions according to the invention are therefore particularly well suited for use in surfactant-containing perfumed articles.

It is preferred if the perfumed article is one of the following:
an acidic, alkaline or neutral cleaner which is selected in particular from the group consisting of all-purpose cleaners, floor cleaners, window cleaners, dishwashing detergents, bath and sanitary cleaners, scouring milk, solid and liquid toilet cleaners, powder and foam carpet cleaners, liquid detergents, powder detergents, laundry pretreatments such as bleaches, soaking agents and stain removers, fabric softeners, washing soaps, washing tablets, disinfectants, surface disinfectants,
an air freshener in liquid form, gel-like form or a form applied to a solid carrier or as an aerosol spray,
a wax or a polish, which is selected in particular from the group consisting of furniture polishes, floor waxes and shoe creams, or
a body care composition, which is selected in particular from the group consisting of shower gels and shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics.

The customary ingredients with which fragrances used according to the invention, or inventive fragrance compositions, may be combined, are generally known and described for example in PCT/EP2015/072544, the teaching of which is hereby expressly incorporated by reference.

EXAMPLES

The examples below are intended to illustrate the invention in more detail. The percentages in the examples are weight percentages unless otherwise indicated.

Determining the mean particle diameter in aqueous suspension/emulsion using light scattering: The particle diameter of the w/o/w emulsion or the particle suspension is determined with a Malvern Mastersizer 2000 from Malvern Instruments, England, sample dispersion unit Hydro 2000S according to a standard measurement method which is documented in the literature. The value D[4,3] is the volume-weighted average.

Determining the Mean Particle Diameter of the Solid:

The microparticles are determined as powder with a Malvern Mastersizer 2000 from Malvern Instruments, England, including powder feed unit Scirocco 2000 according to a standard measurement method which is documented in the literature. The value D[4,3] is the volume-weighted average.

Determining the Pore Diameter:

The pore diameters were determined by means of scanning electron microscopy (Phenom Pro X). For this purpose, various close-up images were taken and these were retrospectively automatically measured using the ProSuite (FibreMetric) software from Phenom. The pores of a selected region of a particle were identified using the difference in contrast and the surfaces thereof were automatically measured. The diameter for each surface was calculated with the assumption that the surfaces were circular. (Sample size 100 pores).

In the context of the evaluation, only those pores whose pore diameter was at least 20 nm were taken into consideration. Depending on the particle size, the images were recorded, for larger particles with 1600- to 2400-times magnification, and for smaller particles with up to 8000-times magnification.

In order to determine the size of at least 10 pores, only those microparticles whose particle diameter does not deviate from the mean particle diameter of the composition of microparticles by more than 20% were taken into consideration.

The following assumptions were made for evaluation of the number of pores based on the total surface area of the microparticle: Since these are spherical particles, the image only shows half the surface of the particle. If the image of a microparticle shows at least 5 pores whose diameter is at least 20 nm and whose diameter is in the range from 1/5000 to 1/5 of the mean particle diameter, then the total surface comprises at least 10 pores.

The evaluation was carried out according to the following procedure:

1. The mean particle diameter D[4,3] of the microparticles was already determined in the microparticle dispersion, using light scattering. The upper and lower limits of the particle diameter of the microparticles which are taken into consideration for determining the pores (±20%) can be calculated from this.
2. The microparticle dispersion was dried.
3. From a sample, in each case 20 images showing multiple microparticles were taken by means of scanning electron microscopy.
4. 20 microparticles were selected whose particle diameter is in the range ±20% of the mean particle diameter of the microparticles. The particle diameter thereof was thus measured with the ProSuite (FibreMetric) software from Phenom.
5. The pores of each of these 20 microparticles were measured. For this purpose, the surface areas of the visible pores were measured automatically and the diameter thereof was calculated.
6. The individual values of the pore diameters were checked as to whether their diameter met the condition of being in the range from 1/5000 to 1/5 of the mean particle diameter and being at least 20 nm.
7. The number of pores meeting this condition was determined and multiplied by two.
8. It was verified whether at least 16 microparticles had on average at least 10 pores.

Determining the Bulk Density:

The bulk density was determined as specified in DIN-EN ISO 60: 1999;

Determining the Water Content of the Microparticle Composition

Karl Fischer titration (DIN 51777): For this, approx. 2 g of powder were precisely weighed in and titrated with a 799 GPT titrino by the Karl-Fischer method.

Abbreviations:
PBSeT—polybutylene sebacate terephthalate
PBAT—polybutylene adipate terephthalate
PLA—polylactide
PS—polystyrene
PC—polycarbonate
PBA—polybutylene adipate
PLGA—polylactide-co-glycolide
PVA—polyvinyl alcohol Example 1: Procedure for Preparing the Fillable Spherical Microparticles Pore former solution: 0.5 g of ammonium carbonate were dissolved in 54.0 g of water (pore former).

Solution of the aliphatic-aromatic polyester: 21.6 g of PBSeT were stirred into 270.0 g of dichloromethane and dissolved at 25° C. while stirring.

In order to prepare the w/o emulsion, 54.5 g of pore former solution were emulsified in the solution of the aliphatic-aromatic polyester for 1 minute at 10 000 rpm with a rotor-stator.

The resultant w/o emulsion was transferred into the polyvinyl alcohol solution (having a degree of hydrolysis of 88 mol % and a viscosity of 25 mPa*s and proportion of carboxyl groups of 3 mol %) and likewise emulsified with shear and energy input (one minute at 10 000 rpm with a rotor-stator).

The w/o/w emulsion produced in this way was subsequently further stirred at 150 rpm with an anchor stirrer, heated slowly to 40° C. while being stirred, and kept at this temperature for 4 hours with a nitrogen flow of 100 l/hour. Thereafter, the microparticle suspension was cooled to room temperature and freeze-dried.

The particle diameter after freeze-drying was 5 μm,
Water content: 0.5%

Examples 2 to 4 and 6 to 7

Analogously to example 1, fillable spherical microparticles were prepared with the remaining pore formers given in table 1 at the respective concentrations and also the polymer mixtures given in table 1 (made of aliphatic-aromatic polyester and a further polymer).

Example 5

Analogously to example 1, spherical microparticles were prepared, with the difference that for producing the w/o/w emulsion, emulsification was carried out with an anchor stirrer at 150 rpm.

TABLE 1

Fillable spherical microparticles using various pore formers

| Ex. | Pore former | Concentration of pore former [wt %] | Polymer | Mean particle diameter D[4,3] [μm][1] |
|---|---|---|---|---|
| 1 | Ammonium carbonate | 0.5 | PBSeT | 5 |
| 2 | Ammonium hydrogencarbonate | 1.0 | Mixture (55% PBAT with 45% PLA) | 42 |
| 3 | Sucrose | 1.0 | Mixture (55% PBAT with 45% PLA) | 9 |
| 4 | Sucrose | 10.0 | Mixture (55% PBAT with 45% PLA) | 8 |
| 5 | Ammonium sulfate | 40.0 | PBSeT | 200 |
| 6 | Sodium chloride | 10.0 | Mixture (55% PBAT with 45% PLA) | 11 |
| 7 | Ammonium oxalate | 1.0 | Mixture (55% PBAT with 45% PLA) | 48 |

[1] Determining the particle diameter of the microparticle in the aqueous suspension.

Examples 8, 11 and 12

The procedure was conducted analogously to example 1, with the difference that the polymer mixtures found in table 2 were used.

Examples 9 and 10

The procedure was conducted analogously to example 5, with the difference that the polymer mixtures found in table 2 were used.

TABLE 2

Fillable spherical microparticles using various polymers

| Example | Polymer | Mean particle diameter D[4,3] [μm][1] |
|---|---|---|
| 8 | Mixture (55% PBSeT + 45% PLA) | 11 |
| 9 | Mixture 90% PBSeT + 10% PS | 200 |
| 10 | Mixture (70% PBSeT + 30% PC) | 250 |
| 11 | Mixture (50% PBSeT + 50% PBA) | 8 |
| 12 | Mixture (55% PBSeT + 45% PLGA) | 5 |

[1] Determining the particle diameter of the microparticle in the aqueous suspension.

Example 13-20 Preparation of Various Particle Sizes 21.6 g of PBSeT were stirred into 270.0 g of dichloromethane and dissolved at 25° C. while stirring. 54.5 g of pore former solution (5 g ammonium carbonate dissolved in 54.0 g water) were emulsified in this solution for 1 minute at 10 000 rpm with a rotor-stator.

The resultant w/o emulsion was transferred into the polyvinyl alcohol solution (having a degree of hydrolysis of 88 mol % and a viscosity of 25 mPa*s and proportion of carboxyl groups of 3 mol %) and likewise emulsified with shear and energy input (found in table 3).

The w/o/w emulsion produced in this way was subsequently further stirred at 150 rpm with an anchor stirrer, heated slowly to 40° C. while being stirred, and kept at this temperature for 4 hours with a nitrogen flow of 100 l/hour. Thereafter, the microparticle suspension was cooled to room temperature and freeze-dried.

TABLE 3

Emulsification of the w/o emulsion in water to give the w/o/w emulsion

| Example | Emulsifying apparatus | Duration [min] at rpm | Mean particle diameter [μm][1] |
|---|---|---|---|
| 13 | Anchor stirrer | 1 min, 800 rpm | 500 |
| 14 | Rotor-stator | 1 min at 3500 rpm | 130 |
| 15 | Rotor-stator | 1 min at 6000 rpm | 75 |
| 16 | Rotor-stator | 1 min at 10 000 rpm | 6 |
| 17 | Rotor-stator | 1 min at 15 000 rpm | 4 |
| 18 | Rotor-stator | 1 min at 20 000 rpm | 2 |
| 19 | Rotor-stator | 1 min at 26 000 rpm | 2.5 |
| 20 | Ultrasound | 1 min at 400 W, 24 kHz | 1.0 | rpm: revolutions per minute
[1] Determining the particle diameter of the microparticle in the aqueous suspension.

General Procedure: Filling and Closing the Capsules 20 g of the fillable spherical microparticles obtained from example 5 were stirred with 40 g of a solution of an aroma chemical (see table 4) on a roller mixer for five hours.

Subsequently, the entire suspension was heated to 60° C. (jacket temperature) and kept at this temperature for five hours. This suspension was then cooled to room temperature, filtered and rinsed three times with ethanol. Subsequently, the microparticles were dried for four hours in a drying oven at 40° C.

According to this procedure, the filled microparticles of examples 21 to 23 were obtained.

The loading of the microparticles was calculated as follows:

Loading [%]=(weight loaded *M*–weight unloaded *M*)·100/weight loaded *M*

M: microparticles

TABLE 4

| Example | Aroma chemical | Solvent | Concentration of the aroma chemical [wt %] | Loading of the microparticles [%] |
|---|---|---|---|---|
| 21 | L-Menthol | 1,2-propylene glycol | 10 | 44 |
| 22 | Rose Oxide | 1,2-propylene glycol | 10 | 52 |
| 23 | Dihydrorosan | 1,2-propylene glycol | 10 | 50 |

Example 24: Procedure for Preparing Fillable Spherical Microparticles (Small Particles)

Pore Former: Ammonium Sulfate

Solution of the aliphatic-aromatic polyester: 1.8 g of PBSeT were stirred into 22.5 g of dichloromethane and dissolved at 25° C. while stirring.

In order to prepare the w/o emulsion, 4.5 g of a 0.5% pore former solution were emulsified in the solution of the aliphatic-aromatic polyester for 1 minute at 10 000 rpm with a rotor-stator.

The resultant w/o emulsion was transferred into the polyvinyl alcohol solution (having a degree of hydrolysis of 88 mol % and a viscosity of 25 mPa*s and proportion of carboxyl groups of 3 mol %) and likewise emulsified with shear and energy input (one minute at 8 000 rpm with a rotor-stator).

The w/o/w emulsion produced in this way was subsequently further stirred at 400 rpm with an anchor stirrer and kept at 25° C. for 4 hours with a nitrogen flow of 60 l/hour.

The mean particle diameter of the microparticles D[4,3] was 11.1 µm. Pores were only measured from those microparticles whose particle diameter was in the range from 9.99 to 12.21 µm as determined by scanning electron microscopy. The lower limit calculated for pores that met this condition was 0.02 µm and the upper limit was 2.22 µm. Evaluation of the SEM images showed that the measured microparticles each had more than 5 pores in the image that met the condition, and thus on average more than 10 pores on the surface of each microparticle. The number of pores was also met for the preferred pore size range 4/100 to 1/5 of the mean particle diameter (calculated lower and upper limits: 0.44 µm to 2.22 µm).

Examples 25-28

Analogously to example 5, spherical microparticles were prepared, with the difference that the pore formers given in table 5 were used instead of ammonium sulfate.

TABLE 5

Fillable spherical microparticles using various pore formers

| Ex. | Pore former | Concentration of pore former [% by wt.] | Polymer | Mean particle diameter D [4,3] [1] [µm] |
|---|---|---|---|---|
| 25 | Ammonium carbonate | 1.0 | Mixture (55% PBAT with 45% PLA) | 150 |
| 26 [2] | — | 1.0 | Mixture (55% PBAT with 45% PLA) | 104 |
| 27 | — | — | Mixture (55% PBAT with 45% PLA) | 155 |
| 28 | Ammonium carbonate | 0.25 | Mixture (55% PBAT with 45% PLA) | 399 |

[1] Determining the particle diameter of the microparticle in the aqueous suspension.
[2] Water-soluble pore formers were not used, rather the surfactant sorbitan monooleate (Span 80) was used.

TABLE 6

Detailed characterization of spherical microparticles using various pore formers

| Ex. | Mean particle diameter [µm] | Smallest and largest pore diameter measured [µm] | | Calculated upper and lower limits of the pore diameter [µm] | | Number of pores ≥10 |
|---|---|---|---|---|---|---|
| | | min | max | Lower limit [1] | Upper limit [2] | |
| 25 | 150 | 0.3 | 4.94 | 0.03 | 30.0 | Met |
| 26 | 104 | 2.0 | 12.8 | 0.02 | 20.8 | Met |
| 27 | 155 | 0.3 | 2.8 | 0.31 | 31.0 | Met |
| 28 | 399 | 0.9 | 6 | 0.08 | 79.8 | Met |

[1] 1/5000 of the mean particle diameter of the microparticles
[2] 1/5 of the mean particle diameter of the microparticles

Examples 29-31: Filling and Closing the Microparticles 20 g of each of the fillable spherical microparticles obtained from examples 25-27 were stirred with 40 g of a solution of an aroma chemical mixture on a roller mixer for five hours. Subsequently, the entire suspension was heated to 60° C. and kept at this temperature for five hours. This suspension was then cooled to room temperature, filtered and rinsed three times with a 10 wt % aqueous propanediol solution. Subsequently, the microparticles were dried for four hours in a drying oven at 40° C.

The loading of the microparticles was calculated as follows:

Loading [%]=(weight loaded $M$−weight unloaded $M$)·100/weight loaded $M$

M: microparticles

TABLE 7

Filling

| Example | Capsules used (example no.) | Loading of the microparticles [%] |
| --- | --- | --- |
| 29 | 25 | 74 |
| 30 | 26 | 65 |
| 31 | 27 | 69 |

The filled microparticles according to the invention demonstrate good loading. Furthermore, they have good storability, especially with respect to moisture. The preferred microparticles with small pores of examples 25 and 27 also especially have good tightness.

The invention claimed is:

1. A composition consisting essentially of spherical microparticles composed of a wall material and at least one cavity that comprises a gas and/or a liquid, which have pores on the surface thereof, wherein the spherical microparticles have a mean particle diameter of 10-600 gm; and
wherein at least 80% of microparticles whose particle diameter does not deviate from the mean particle diameter of the microparticles of the composition by more than 20%, each have on average at least 10 pores with a diameter in the range from 1/5000 to 1/5 of the mean particle diameter, with the proviso that the diameter of each of the at least 10 pores is at least 20 nm, wherein the wall material is formed of a composition comprising at least one aliphatic-aromatic polyester selected from the group consisting of polybutylene azelate-co-butylene terephthalate (PBAzeT), polybutylene brassylate-co-butylene terephthalate (PBBrasT), polybutylene adipate terephthalate (P BAT), polybutylene sebacate terephthalate (PBSeT) and polybutylene succinate terephthalate (PBST),
wherein the wall material has a solubility in dichloromethane of at least 50 g/l at 25° C.; and wherein the pores are in the walls of the microparticles.

2. The composition of spherical microparticles according to claim 1, wherein the composition forming the wall material comprises at least one polymer having a glass transition temperature or a melting point in the range from 45 to 140° C.

3. The composition of spherical microparticles according to claim 1, wherein the wall material is formed of a composition comprising the at least one aliphatic-aromatic polyester and also at least one further polymer selected from the group consisting of polyacrylate, polyamide, polycarbonate, polystyrene, aliphatic-aliphatic polyester, aromatic-aromatic polyester, polyolefin, polyurea and polyurethane.

4. The composition of spherical microparticles according to claim 1, wherein the wall material is formed of a composition comprising the at least one aliphatic-aromatic polyester and also at least one aliphatic-aliphatic polyester.

5. A carrier substance for filling with at least one aroma chemical comprising the spherical microparticles according to claim 1.

6. A perfume, washing or cleaning agent, cosmetic agent, body care agent, hygiene article, food, food supplement, scent dispenser or fragrance comprising the composition according to claim 1.

7. An agent composition comprising the composition according to claim 1, in a proportion by weight of 0.01 to 99.9 wt % based on the total weight of the composition.

8. A method for controlled release of aroma chemicals comprising utilizing the composition according to claim 1.

9. A liquid suspension comprising the composition according to claim 1.

10. The liquid suspension of according to claim 9, wherein the spherical microparticles are suspended in an aqueous suspension.

11. The composition according to claim 1, wherein the wall material is formed of a composition comprising the at least one aliphatic-aromatic polyester and at least one further polymer is selected from the group consisting of polyacrylate, polyamide, polycarbonate, polystyrene, aliphatic-aliphatic polyester, aromatic-aromatic polyester, polyolefin, polyurea, and polyurethane, and wherein the proportion of the at least one aliphatic-aromatic polyester is 30 to 99 wt % based on the total weight of the at least one aliphatic-aromatic polyester and the at least one further polymer.

12. The composition of spherical microparticles according to claim 11, wherein the aliphatic-aliphatic polyester is selected from the group consisting of polylactide, polylactic acid copolymers, and poly(lactic-co-glycolic acids).

* * * * *